(12) United States Patent
Trescony et al.

(10) Patent No.: US 7,122,027 B2
(45) Date of Patent: Oct. 17, 2006

(54) IMPLANTABLE MEDICAL DEVICE WITH CONTROLLABLE GASEOUS AGENT RELEASE SYSTEM

(75) Inventors: Paul V. Trescony, Champlin, MN (US); Kenneth E. Rohly, Lino Lakes, MN (US); James R. Keogh, Maplewood, MN (US); Darrell F. Untereker, Cedar, MN (US); Naim S. Istephanous, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 826 days.

(21) Appl. No.: 10/155,296

(22) Filed: May 23, 2002

(65) Prior Publication Data

US 2003/0009127 A1    Jan. 9, 2003

(51) Int. Cl.
*A61M 37/00* (2006.01)
(52) U.S. Cl. .................. 604/891.1; 604/23; 604/26; 604/288.01
(58) Field of Classification Search ............ 604/23–26, 604/288.01–288.04, 890.1, 891.1, 93.01, 604/65–67, 96.01–103.14, 131, 145–146, 604/151; 424/422–425
See application file for complete search history.

(56) References Cited

U.S. PATENT DOCUMENTS

| | | | | |
|---|---|---|---|---|
| 3,336,919 A | * | 8/1967 | Clem | 600/355 |
| 3,878,564 A | * | 4/1975 | Yao et al. | 604/5.04 |
| 3,915,742 A | * | 10/1975 | Battles et al. | 429/102 |
| 4,013,074 A | * | 3/1977 | Siposs | 604/891.1 |
| 4,373,527 A | * | 2/1983 | Fischell | 604/891.1 |
| 4,392,848 A | | 7/1983 | Lucas et al. | 604/53 |
| 5,004,455 A | | 4/1991 | Greenwood | 604/43 |
| 5,149,413 A | * | 9/1992 | Maget | 204/258 |
| 5,154,165 A | | 10/1992 | Elliott et al. | 128/419 R |
| 5,338,412 A | | 8/1994 | Burk | 204/59 R |
| 5,396,882 A | | 3/1995 | Zapol | |
| 5,423,454 A | * | 6/1995 | Lippman et al. | 222/1 |
| 5,458,627 A | | 10/1995 | Baranowski et al. | 607/51 |
| 5,462,644 A | | 10/1995 | Woodson | 204/131 |
| 5,470,307 A | | 11/1995 | Lindall | |
| 5,523,092 A | | 6/1996 | Hanson et al. | 424/423 |
| 5,536,241 A | | 7/1996 | Zapol | |
| 5,578,022 A | | 11/1996 | Scherson | 604/304 |
| 5,582,170 A | | 12/1996 | Soller | |
| 5,648,101 A | | 7/1997 | Tawashi | |
| 5,662,625 A | * | 9/1997 | Westwood | 604/305 |
| 5,662,689 A | | 9/1997 | Elsberry et al. | 607/5 |
| 5,670,664 A | | 9/1997 | Kao | |

(Continued)

FOREIGN PATENT DOCUMENTS

DE    197 15 952 A1    10/1997

(Continued)

OTHER PUBLICATIONS

Hou, Y-C. et al, 214th ACS National Meeting, Las Vegas, NV; Sep. 7-11, 1997; MEDI 039.

(Continued)

*Primary Examiner*—Nicholas D. Lucchesi
*Assistant Examiner*—Melissa A. McCorkle
(74) *Attorney, Agent, or Firm*—David P. Ruschke; Kenneth J. Collier (57) ABSTRACT

The present invention generally relates to medical devices. Specifically, the invention pertains to implantable medical devices that produces gaseous agents from precursors and releases them into the body. More specifically, the invention provides for the controlled release of the gaseous agent to the body to produce a local or systemic therapeutic effect.

17 Claims, 2 Drawing Sheets

U.S. PATENT DOCUMENTS

| | | | |
|---|---|---|---|
| 5,733,572 A | 3/1998 | Unger et al. | 424/450 |
| 5,770,645 A | 6/1998 | Stamler et al. | 524/419 |
| 5,788,682 A | 8/1998 | Maget | 604/290 |
| 5,797,872 A | 8/1998 | Ogata et al. | 604/49 |
| 5,797,887 A | 8/1998 | Rosen | |
| 5,810,015 A * | 9/1998 | Flaherty | 128/897 |
| 5,827,420 A | 10/1998 | Shirazi | |
| 5,869,538 A | 2/1999 | Van Liew et al. | |
| 5,888,528 A | 3/1999 | Wellinghoff | |
| 5,951,458 A | 9/1999 | Hastings et al. | 600/3 |
| 5,951,538 A | 9/1999 | Joshi et al. | 604/500 |
| 5,994,444 A | 11/1999 | Trescony | |
| 6,179,804 B1 | 1/2001 | Satterfield | 604/23 |
| 6,180,059 B1 | 1/2001 | Divino, Jr. | 422/45 |
| 6,238,365 B1 | 5/2001 | Gord et al. | 604/26 |
| 6,312,647 B1 | 11/2001 | Lynch et al. | 422/48 |
| 6,454,566 B1 | 9/2002 | Lynch et al. | 433/80 |
| 6,454,997 B1 | 9/2002 | Divino, Jr. | 422/44 |
| 6,464,687 B1 * | 10/2002 | Ishikawa et al. | 604/891.1 |
| 6,482,309 B1 | 11/2002 | Green et al. | 205/619 |
| 6,520,936 B1 | 2/2003 | Mann | 604/141 |
| 6,632,194 B1 | 10/2003 | Mehner et al. | 604/26 |
| 2001/0020145 A1 | 9/2001 | Sutterfield et al. | 604/24 |
| 2002/0098246 A1 | 7/2002 | Howes | 424/613 |
| 2002/0115559 A1 | 8/2002 | Batchelar et al. | 502/159 |
| 2002/0138034 A1 | 9/2002 | Derek | 604/6.14 |
| 2002/0160053 A1 | 10/2002 | Yahagi et al. | 424/600 |
| 2002/0188323 A1 | 12/2002 | Penner et al. | 607/2 |
| 2003/0065292 A1 | 4/2003 | Darouiche et al. | 604/265 |
| 2003/0104342 A1 | 6/2003 | Lynch et al. | 433/224 |
| 2003/0130614 A1 | 7/2003 | Johnson | 604/35 |
| 2003/0133881 A1 | 7/2003 | Lynch et al. | 424/49 |
| 2004/0022744 A1 | 2/2004 | Lynch et al. | 424/49 |

FOREIGN PATENT DOCUMENTS

| | | |
|---|---|---|
| DE | WO 99/65538 | 12/1999 |
| WO | WO 9831420 | 7/1998 |
| WO | WO 99/07346 | 2/1999 |
| WO | WO 9909912 | 3/1999 |
| WO | WO 00/74743 | 12/2000 |
| WO | WO 03/002243 | 1/2003 |
| WO | WO 03/011170 | 2/2003 |
| WO | WO 03/015839 | 2/2003 |
| WO | WO 03/049660 | 6/2003 |
| WO | WO 03082392 | 10/2003 |

OTHER PUBLICATIONS

Hou, Yunchun, et al, Bioorg. Med. Chem. Lett (1998) 2(21), 3065-3070.

McGill, A., 214th ACS National Meeting, Las Vegas, NV; Sep. 7-11, 1997.

McGill, Andrea D., et al, Methods Enzymology (1999); 301 (Nitric Oxide, Part C: Biiological and Antioxidant Activities), 235-242.

McGill, Andrea D., et al, 212th ACS National Meeting, University of Miami, Aug. 25-29, 1996.

Tuck, Modern Battery Technology by C.D.S.; Li-CFx battery; pp. 337-348.

Wang, Peng G., et al, Portland Press Proc (1996) 10; (Biology of Nitric Oxide Part 5), 190.

Yongchun, H. et al, The Royal Society of Chemistry 2000; pp. 1831-1832.

Hou, Y. et al, 214th ACS National Meeting, Las Vegas, NV; Sep. 7-11, 1997.

Tuck, Modern Battery Technology by C.D.S.

Wang, Peng G., et al, Portland Press Proc (1996) 10.

* cited by examiner

IMPLANTABLE MEDICAL DEVICE WITH CONTROLLABLE GASEOUS AGENT RELEASE SYSTEM

FIELD OF THE INVENTION

The present invention generally relates to medical devices. Specifically, the invention pertains to implantable medical devices that produces gaseous agents from precursors and releases them into the body. More specifically, the invention provides for the controlled release of the gaseous agent to the body to produce a local or systemic therapeutic effect.

BACKGROUND OF THE INVENTION

Classically, use of helium as a substitute for nitrogen in the breathing gas during deep sea diving is well known. The helium prevents nitrogen from dissolving in body fluids at high concentration under pressure. This results in the painful condition known as "the bends", which is one of the first known examples of medical therapy using a gaseous agent.

Oxygen and other anesthetic gases and liquids are now routinely used for therapeutic purposes. Generally, gases are inhaled directly into the body directly. More recently, with the advent of open-heart surgery, oxygen has been administered to the body via extracorporeal blood oxygenators. Further, in the last decade, another gas, nitric oxide, was found to have potent vessel dilatory activity.

Most gases that could be considered for therapeutic applications are hydrophobic low molecular weight compounds of low water solubility. These gases are considered to have the ability to rapidly move through tissue by virtue of their high diffusivity and to cross the lipid membranes of target cells by virtue of their hydrophobic character. This is in contrast to movement of other bioactive agents such as ions, peptides and hormones, whose entry into cells requires specific interactions with cell surface receptors and/or similar transport mechanisms such as ion channeling, endocytosis or pinocytosis.

The mobility of most gaseous agents is between that of the extremely small and rapid acting electron delivered for cardiac pacing or neuro-stimulation therapies and that of slower acting, higher molecular weight agents such as hormones, peptides and molecular biological vectors. The primary delivery route used in gaseous therapy has been through use of extracorporeal devices for inhalation into the lung or to exchange gases in the blood, such as with a blood oxygenator.

The traditional and most widely used means for delivering a gas to the body is by inhalation. Nitrous oxide, xenon, or vapors of highly volatile liquids such as isoflurane are inhaled to produce systemic analgesia or anesthesia. The oxygen concentration of the inhaled gas stream may also be adjusted during anesthesia or during other medical procedures to improve blood oxygenation. Nitric oxide can also be beneficially administered via inhalation to improve lung ventilation by virtue of its vasodilating effect within the alveoli. The physiological effects of inhaled nitric oxide, with a half-life of seconds or less in the body, are limited to the lung while anesthetic gases produce more systemic effects because of their longer half-lives.

As seen from the previous description, the art describes various modalities of producing gaseous agents for delivery though an extracorporeal devices. The present invention provides an important advancement in the art by providing an internal implantable device for generating gaseous agents and their use in therapy. More specifically, the present invention provides a fully implantable medical device system for controlled delivery of a gaseous agent for therapeutic use. Optionally these devices can be integrated with other implantable medical devices. Having a local implantable source of gaseous agent provides a means for better controlled local delivery to the targeted tissue and use of lower concentrations of the gaseous agent.

SUMMARY OF THE INVENTION

One object of the present invention is to provide an implantable medical device for the delivery of gaseous agent. In one embodiment the gaseous agent is generated from stored precursors that are converted to their therapeutic form in an chemical cell. In one embodiment the chemical cell is an electrochemical cell. In another emodiment the chemical cell is a photochemical cell.

The present invention provides a system in which diffusion through the boundaries of an implanted medical device is implemented to deliver a gaseous agent into the body. This method for delivering a gas internally, in cooperation with an implantable medical device, provides a new and enhanced use of therapeutic systems to deliver agents at a smaller, more localized target. More specifically, the invention discloses a fully implantable medical device system for the controlled delivery of a gaseous agent within the body. Further, the invention provides various options in which the therapeutic delivery system could be integrated with other implanted medical devices such as sensors, drug pumps and a number of other implantable devices, to provide an integrated therapy to a patient.

Another object of the invention is provide a means to more directly administer gaseous agents to a targeted tissue. One feature of targeted delivery of gases is the reduction or elimination of systemic effects by gases delivered systemically, as would occur by inhalation or by extracorporeal oxygenators. Another feature of targeted delivery of gaseous agents is that gaseous agents having a short-life, such as nitric oxide, can be more effectively delivered to targeted sites (such as the spinal column, heart, and brain).

An additional object of an implantable device is that it provides for more effective use of gases having longer half-lives (such as most anesthetic gases), whether used locally or systemically. Internal delivery of gasesous agents provides the ability to use the delivered gaseous agent at a lower concentration. Delivery of gaseous agents at lower concentrations will help reduce systemic side effects

DESCRIPTION OF THE DRAWINGS

FIG. 1 (FIG. 1) is a schematic of an implantable medical device for delivery of therapeutic gases consisting of:

- An implantable chemical cell (1) that generates a gaseous agent within the device that contains suitable electrodes or a light source.
- An energy- storage component (2) for delivering or receiving an electrical current from the chemical cell (1)
- An energy controlling component (3) that serves to control the electrical or light energy delivered from the chemical cell (1) thereby controlling the production of the gaseous agent generated within the chemical cell (1). The energy controlling component may be a timer or a switch under external control.
- An optional pair of biocompatible electrical leads (7) from the energy storage/controller component to the chemical cell.

An optional sensor component (4) that senses a physiologically relevant functional parameter(s) of the patient, the sensor component providing an output signal to the energy controlling component (3) in response to the functional parameter(s) sensed.

Optional additional implanted medical device components (5) that could include, but not limited to a catheter, lead, cardiac pacemaker or defibrillator, non-cardiac electrical stimulator, stent, a heart valve, a vascular graft, bioprosthesis, synthetic prosthetic implant, artificial organ, sensor (either (4) or an additional sensor), or a drug pump (6).

Optional interrogation, control and/or reprogramming of release parameters by telemetry with external devices.

Optional electrical circuit from redox reaction of the electrochemical cells to charge or recharge the energy storage device.

In one embodiment, in a highly simplified version, a therapeutic gaseous agent would be located in a reservoir such as a catheter tip, placed at the location appropriate for the intended application (FIG. 1). The therapeutic gas could be contained within the reservoir as a convertible gaseous precursor. Application of a form of regulated energy such as electrical, optical or other energy form to the catheter tip would cause the therapeutic gas to be delivered from the reservoir into the body by passive or active diffusion across the boundary material of the reservoir.

DETAILED DESCRIPTION OF THE INVENTION

The present invention relates to an implantable device that produces gaseous agents that can be utilized therapeutically. The term gaseous agents includes both volitale gases as well as gases dissolved in a fluid medium. In context of the present invention the gaseous agents are initially stored as gaseous precursors, whether in solid, liquid or in gaseous form, or combinations thereof, which are then are transformed to their active and therapeutically use form upon a electrochemical or photochemical transformation of the precursor.

The gaseous agents produced with the present invention are internal delivered with in the body of patient in need thereof. The gaseous agents of the present invention include small molecular weight gaseous compound in aerosol or a dissolved in a fluid medium. For the purpose of this invention, volatile gases are defined to be a volatile gas with a vapor pressure equal to or greater than one greater than 1 millimeter of mercury (Hg) at 37° C. that can be administered to the body as a gas at a rate sufficient to produce a local or systemic therapeutic effect. The method of delivery of these gases can also be adapted to non-gaseous small ions or low molecular weight compounds dissolved in a delivered fluid medium.

For purposes of comparison, a ranking of local drug delivery agents by size is given below. The underlined agents have vapor pressures approximately equal to or greater than 1 millimeter of mercury. Examples of these gases include, but are not limited to, NO, CO, $N_2O$, $N_2$, $O_2$, $O_3$, $CO_2$, $H_2S$, $NH_3$, $H_2O_2$, OH, $H_2S$, $SF_6$, and the like. Most are low molecular weight, non-ionic compounds capable of rapid transit through thin polymeric membranes by passive diffusion alone. Further, most of the gaseous agents are, or are potentially, able to be generated by applying an electrochemical, optical, other controllable form of energy to a simple, storable precursor. Furthermore, many of the gaseous agents are highly potent and biologically active. Although some gases may not therapeutically useful when inhaled, they may have novel therapeutic uses if delivered internally and locally in small controlled doses.

The term "gaseous agent precursor" or "gaseous precursor" refers to the chemical structure of the compound holding an activatable gaseous agent. The gaseous precursor denotes compounds which, at selected activation by light or electrical energy, the precursor, at a defined rate, is converted into a gaseous agent, whether aerosolized or dissolved in a liquid medium. Use of gaseous precursor compounds in context of the electrochemical cell are compounds that require either oxidation or reduction of the compounds to generate a gaseous agent. The term gaseous agent precursor in context of the photochemical cell requires absorbance of the appropriate light energy to activate the production of the gaseous agent.

The term "electrochemical cell" or "electrolytic cell" refers to a composite containing an anode, a cathode and an ion-conducting electrolyte interposed therebetween. Such an electrochemical cell, is made from at least one pair of asymmetric electrode assemblies. As used herein, the term "asymmetric electrodes" means that the two electrodes are not the same composition, i.e. they are made from different materials. Examples of some asymmetric electrodes are anodes made from metal hydrides (MH) or metals such as Al, Bi, Fe, In, Mg, Mn, Pb, Sb, Sn, W, Zn and oxides, hydroxides or alloys thereof. Cathodes may be made from Ag, Au, Co, Cr, Cu, Fe, Mn, Mo, Ni, Pb, V, W and oxides, hydroxides or alloys thereof These materials are simply presented by way of example and are not intended to limit the scope of the claims. Each electrode assembly may optionally include a current collector which is electrically conducting that serves to return collected energy to charge or recharge a energy storage component or battery. A housing or gasket may be employed to house the electrodes and the electrolyte, but is optional. The electrolyte that is sandwiched between the electrodes is in the form of a film, solution, or gel, and any other materials known in the art which serves as a separator between the electrodes, capable of affording free and unobstructed movement to the ions in the electrolyte. The combination electrolyte/separator prevents contact between the opposing electrodes, since such a condition would result in a short circuit and malfunction of the cell. The electrolyte may also be used in conjunction with a conventional separator, and in that embodiment it is impregnated into a porous separator. Materials useful for a porous separator are well known to those skilled in the art, including porous versions of polymers such as polyvinylchloride, polypropylene, and cellulose acetate, filter paper, felt, and other types of similar materials. The separator is typically saturated with the electrolyte while the electrolyte is still in the liquid form.

The term "energy source" or "battery" or refers to two or more electrochemical cells electrically interconnected in an appropriate series/parallel arrangement to provide the required operating voltage and current levels to the chemical cell where required. It is recognized that some electrochemical reactions within the scope of the present invention do not require a voltage source, while other do, depending on E° of the particular electrochemical reaction. Where the compounds are photosensitive, the energy source provides sufficient energy to cause the light source to irradiate at the appropriate wave length. It is recognized that an energy source or battery can also serve as an energy storage component to store energy produced from a electrochemical cell.

The present invention contemplates delivery of the therapeutic gaseous agents by various methods and systems. When the gaseous agent is produced it may be used directly or mixed with other gases or dissolved into solution to a concentration necessary to produce a beneficial effect. When the agent is produced from a liquid or solid, it can be delivered as part of a gas mixture at a partial pressure below its ambient vapor pressure. Accordingly, gaseous agents can be delivered to the body by diffusion into the blood through a blood contacting surface or by diffusion, into the surrounding tissue through the boundaries of an implanted medical device.

Integrated Systems for Delivery

Therapeutic gases are often highly potent and their activities are integrated with other long-term variable physiological responses. Chronic, tightly regulated delivery of small quantities of gaseous agents under physiological, patient, or preset control will often be required. The need for chronic, on-demand delivery makes a fully implantable system with integrated sensing, control, and delivery functions very desirable. For example, in order to treat angina or to reduce the incidence of defibrillation events associated with implantable cardiodefibrillator therapy it would be desirable to deliver nitric oxide or carbon monoxide to the coronary vasculature within seconds to minutes of sensing the need for such therapy. This therapy could be linked to physiological sensing and/or patient activation. Other potential applications include but are not limited to, the control of urinary voiding, digestive tract motility, or modulation of uterine contractility to inhibit pre-term labor. For the treatment of impotence, nitric oxide or carbon monoxide would be delivered under patient control.

In yet another case, the optical response of an indwelling blood gas sensor might be stabilized by releasing nitric oxide near the sensor window to inhibit platelet-derived thrombus formation. Here, it may be desirable to release nitric oxide continuously at a variable rate or intermittently according to sensor performance. Anesthetic gases could be delivered to specific target nerves to provide chronic pain relief with the release controlled by patient demand subject to device-controlled limitations on the dosing frequency and a time-weighted maximum amount delivered. Variable and/or on-demand delivery will also optimize the therapeutic effectiveness and minimize the side effects associated with the gaseous agent and will extend the device lifetime by conserving the supply of gaseous agents or precursors within the implantable device.

The present invention operates in cooperation with, gaseous agent precursor in, an implantable medical device in which, atomic particles, small ions, small neutral molecules, low molecular weight compounds, high molecular weight compounds, microscopic as therapeutic agents or mediums through which gaseous agents that can be released into the body. Generally, the therapeutic agents that are contemplated by the present invention could be generated using light, including UV invisible light or infrared.

Methods of delivery include, but are not limited to, external systemic, external local, internal systemic, internal local, and combinations of external, internal, systemic and local delivery systems.

Therapeutic Uses

Current uses of therapeutic gases—anesthetic gases: Anesthetic gases can produce effects ranging from reducing anxiety to analgesia to anesthesia. In general these effects are thought to result from the interaction of the anesthetic gas with a variety of neural cell receptors (GABAnergic, glycinergic, NMDA, glutamate, or adenosine) and/or with cellular ion-channel gates (sodium, potassium or calcium channels. Nitrous oxide ($N_2O$) has been shown to produce analgesia in part by stimulating release of analgesic peptides called endorphins from endogenous stores.

Gaseous anesthetic agents can also produce other physiological effects. For example, cerebral or cardiac blood vessels can dilate or constrict depending on the anesthetic gas and dosage administered. Anesthetic gases are being tested as neuro-protecting agents for the brain or spinal cord following trauma injury based on their ability to reduce post-ischemic neutrophil adhesion to the endothelium. Anesthetic gases are also known to provide cardio-protective benefits to the heart similar to that seen after ischemic preconditioning. As a result anesthetic gases may be useful for a variety of non-anesthetic purposes when introduced locally to non-lung sites. Gases such as nitric oxide, carbon monoxide, hydrogen sulfide, and hydrogen cyanide may even find therapeutic use when delivered at levels that are locally but not systemically cytotoxic to treat tumors or remove or ablate unwanted tissue.

Current uses of therapeutic gases—blood gases ($O_2$ and $CO_2$): The saturation level of oxygen and carbon dioxide in the blood and in tissue beds has a profound effect on the metabolic and proliferative activity of cells and tissues. Blood gases also exert other effects not directly related to cellular respiration. For example, a hypoxic state within the heart can induce local tissue death, promote ischemic pre-conditioning and/or induce angiogenesis depending on the degree and rate of onset of hypoxia. The blood gases, oxygen, carbon dioxide or even nitrogen might be locally delivered to stimulate angiogenesis or to promote site-specific healing or tissue development. Controlled delivery of low concentrations of these gases may serve to augment angiogensis.

Current uses of therapeutic gases—nitric oxide and carbon monoxide: Nitric oxide and carbon monoxide were primarily thought of as highly toxic products of combustion until the last decade. Subsequently it has been discovered that these two gases are actually biologically important endogenous molecules. At nanomolar to micromolar concentrations, these gases mediate a variety of important biological functions including vascular tone, hemostasis, cell proliferation and neuronal signaling. This realization has led to numerous efforts to use these gases, particularly nitric oxide, for therapeutic purposes. The lung remains the primary site for delivering these gases directly while methods for delivering these agents internally to other sites have focused on delivery of non-gaseous precursors.

Nitric oxide is extremely labile in vivo existing with a half-life of a few seconds or less in the blood. It is also extremely potent, acting upon a variety of cell types at nanomolar to micromolar concentrations. Nitric oxide can be formed from a number of adducts. These nitric oxide containing adducts are thought to increase the bioactivity of nitric oxide by virtue of their increased lifetimes. Nitric oxide binding to hemoglobin has recently been shown to be interactive with oxygen binding to the heme center of the hemoglobin molecule. This binding is reversible and may contribute to the local regulation of both nitric oxide and oxygen levels within tissue analogous to the interactive binding of the oxygen and carbon dioxide to hemoglobin. Carbon monoxide is generated when the enzyme heme oxygenase acts on red blood cell-derived heme as part of the catabolic pathway for heme-containing molecules. Carbon monoxide formed is a potent vasodilator that acts biochemically in a manner analogous to nitric oxide. The liver has been shown to release both carbon monoxide and nitric oxide as part of its normal physiological function. Because nitric oxide and carbon monoxide as well as the blood gases oxygen and carbon dioxide are endogenous metabolites that bind interactively with hemoglobin it may be useful to deliver more than one of these gases.

Additional uses for nitric oxide and/or carbon monoxide might be for delivery to internally treat angina, to prevent restenosis following balloon angioplasty, to treat impotence, to prevent pre-term labor, or to treat asthma and other lung dysfunction. These gases may also be employed internally to prevent a stroke or limit its damage to the brain or to treat memory loss due to trauma or neuro-degenerative diseases. Nitric oxide and/or carbon monoxide might also be used to augment current medical device-based therapies in the area of ICD therapy (by reducing the incidence or moderating the severity of defibrillation events), to improve indwelling sensor performance, or to reduce thrombosis associated with cardiopulmonary bypass. Therapeutic gases such as nitric oxide may also be employed to stimulate secretion of endogenous hormones when targeted to the pancreas or other organ.

Current uses of therapeutic gases—other gases: Many other gases such as nerve gases, hydrogen cyanide, or hydrogen sulfide are of such high toxicity that they are not considered as therapeutic agents when inhaled. However, with sufficient control of the dose delivered and precise delivery to target sites even these highly toxic gases might find therapeutic use in the future for such purposes as the treatment of tumors. It may also be found in the future that gases such as nitrogen or sulfur hexafluoride that are not generally considered to be biologically active when inhaled may also be therapeutically useful when delivered to appropriate internal tissue sites.

Nitrous oxide or another anesthetic gas could be locally targeted to neural tissue to block chronic pain without the systemic effects that would occur with chronic inhalation of the gas. Gases might be delivered directly to regions of the brain to produce specific behavioral effects or modify brain activity for the treatment of Parkinson's disease or epilepsy. Anesthetic gases might also be used as an adjunct to electrical or pharmacological therapies for cardiac rhythm diseases.

More than one gas might be locally delivered to achieve an additive or synergistic effect. For example, a gas with analgesic activity such as nitrous oxide might be delivered in tandem with a vasodilating gas such as nitric oxide for the treatment of angina or for ICD therapy. Carbon monoxide might be delivered together with nitric oxide in order to bind to the heme iron responsible for oxidizing nitric oxide. The lifetime of nitric oxide would then be prolonged allowing for greater diffusion after local delivery.

Redox Generation of Gaseous Agents

Oxygen may be suitably formed electrochemically from a solid anode material of the general form $Z_x O_y$, wherein Z is a Ia or Ib element of the periodic table and the value of x is 1 to 3. O is oxygen and y is 1 to 4. Nitrogen can be electrochemically released from a solid anode material of the general form $A_a N_b$. The value of a is 1 to 3 and b is 1 to 3. In each of the above instances, an ion migrates across a suitable ion conducting electrolyte. The migrating ions may be, respectively, A ions or A' ions. A can be cations such as silver, copper and the like in a positive valence state, while A' is an alkali metal such as sodium, lithium and the like in a positive valence state. The migrating ion (cation) allows the anion ($O_2$ or $N_3$) to combine with a similar anion to form a gas ($O_2$ or $N_2$) concomitant with the release of electrons. At the cathode, several possibilities may occur; examples include ones in which the migrated cations are reduced to their elemental state, or where a solid material $R_2$ wherein R is a halogen is ionizable to $R^-$, or solid material, R', where R' is a group VIB element reducible to $R'^{-2}$ or where cathode material CRx is reduced to C+XR−. A typical CRx is a fluorocarbon such as a CFx which is readily available. In the above formulas, X and x are equivalent and have a value of about 0.8 to about 1.2. The driving force powering the device is either provided by the electrochemical reactions occurring during operation of the cell, or by a battery Electrochemical generation of nitric oxide may be obtained from substituted N-nitroso-N-oxybenzenamine ammonium salts. (McGill, A., 214th ACS National Meeting, Las Vegas, Nev., Sep. 7–11 (1997)). The N-Nitroso-N-oxybenzamine ammonium salts with —OMe, —Me, —H, —Cl, —CF$_3$, and —SO$_2$Me substituents at the para position of the pheny ring constitute a class of redox sensitive nitric oxid (NO) releasing compounds. Oxidation of these compounds via electrolysis provided for NO generation. Threshold potential values ranged from approximately 350 mV vs. Ag/AgCl for —OMe substituted N-nitroso-N-oxybenzeamine ammonium salt, to approximately 700 mV for the —SO$_2$Me substituted compound. N-Hydroxyl-N-nitrosobenzeamines also can be electrochemically oxidized to generate nitric oxide (Wang, Peng G., et al., Portland Press Proc. (1996), 10(Biology of Nitric Oxide Part 5). Para substituted N-hydroxy-N-nitrosaminobenzenes are also able to be electrochemically oxidized to generate nitric oxide (NO).

Similarly, electrochemical reduction of S-nitrosothiols, such as S-nitroso-Nacetyl-D-peneicillamine (SNAP), S-nitrosoglutathione (GSNO) and [N-(β-D-glucopyranosyl)-N2-acetyl-S-nitroso-D, L-penicillaminamide] (1-Glc-SNAP) has been effective to produce nitric oxide in aqueous and organic media(Hou, Y., et al., 214th ACS National Meeting, Las Vegas, Nev., Sep. 7–11 (1997)).

Electrochemical reduction to production of nitric oxide can also be achieved from a preformed chemical layer bonded on the surface of the electrode (Yongchun, H., The Royal Society of Chemistry 2000, 1831–1832).

Photochemical Generation of CO and NO

Caged compounds are molecules in which the presence of a photosensitive masking group conceals the gaseous agent. When the caged molecule is exposed to a flash of light, however, the masking group, or "cage" is photchemically cleaved to restore the bioactivity of the signaling molecule. Using caged compounds allows bioactive substance to be rapidly photo-released in situ.

Light-induced reaction can be used to release carbon monoxide, which is set out in U.S. Pat. No., 5,670,664 which illustrates the use of acetal derivatives of bicyclo[2.2.1] hepta-2,5-diene-8-one for the release of CO upon U.V. irradiation. Several organic caged bis-N-nitroso caged nitric oxide compounds that are photolabile NO donors are commercially available: N,N'-dinitroso-p-phenylenediamine; N,N-dicarboxymethyl-N,N'-dinitroso-p-phenylenediamine, disodium; N,N-dinitroso-p-phneylenediamine-N,N'-diacetic acid; S-Nitroso-N-valeryl-D,penicillamine are available from Molecular Prrobes. Photoliable inorganic NO complexes are also known, such as potassium nitrosylpentachlorouthenate is also available commercially (Molecular Probes Cat. No. P-7070). The spin-trap N-t-butyl-α-phenylnitrone (B-7893) releases NO in aqueous solutions when illuminated with UV or even ambient light. NVOC-caged SIN-1 (Molecular Probes Cat. No. D-7111) is uncaged after UV illumination. Other commercially available photo-liable nitric oxide donors include 2-methyl-2-nitrosopropane dimmer (Molecular Probes M-7905) and S-nitroso-glutathione (Molecular Probes Cat. No. N-7903).

EXAMPLES

Example 1

Construction and Meaurement of Nitric Oxide Release From A Catheter Sized Microelectrode A small-scale (10 ml) electrochemical cell with platinized working and counter electrodes and a silver/silver chloride reference electrode was assembled to evaluate various nitrite-containing solutions for production of nitric oxide from a catheter sized microelectrode. Nitrogen was sparged through the electrochemical cell solutions while a potentiostat applied a preprogrammed voltage ramp to the working and counter electrodes. Nitric oxide generated in the cell was detected in the sparge gas with a chemilumniscent detector. A flowing buffer system was constructed to pass phosphate buffer from a thermostated bath past a glass column containing ports for a nitric oxide-generating microelectrode (ca. 9 French) and an electrochemical detector (sensitive to dissolved nitric oxide). Additional ports allow for the sampling of buffer downstream of the microelectrode for later chemiluminescent measurement of NOx (free NO and nitrite, the oxidative product of NO in oxygenated buffer). A 9 French microelectrode cell with platinized working and counter electrodes and a silver/silver chloride reference electrode was also constructed with a 0.005" thick silicone membrane housing.

Figure 1:
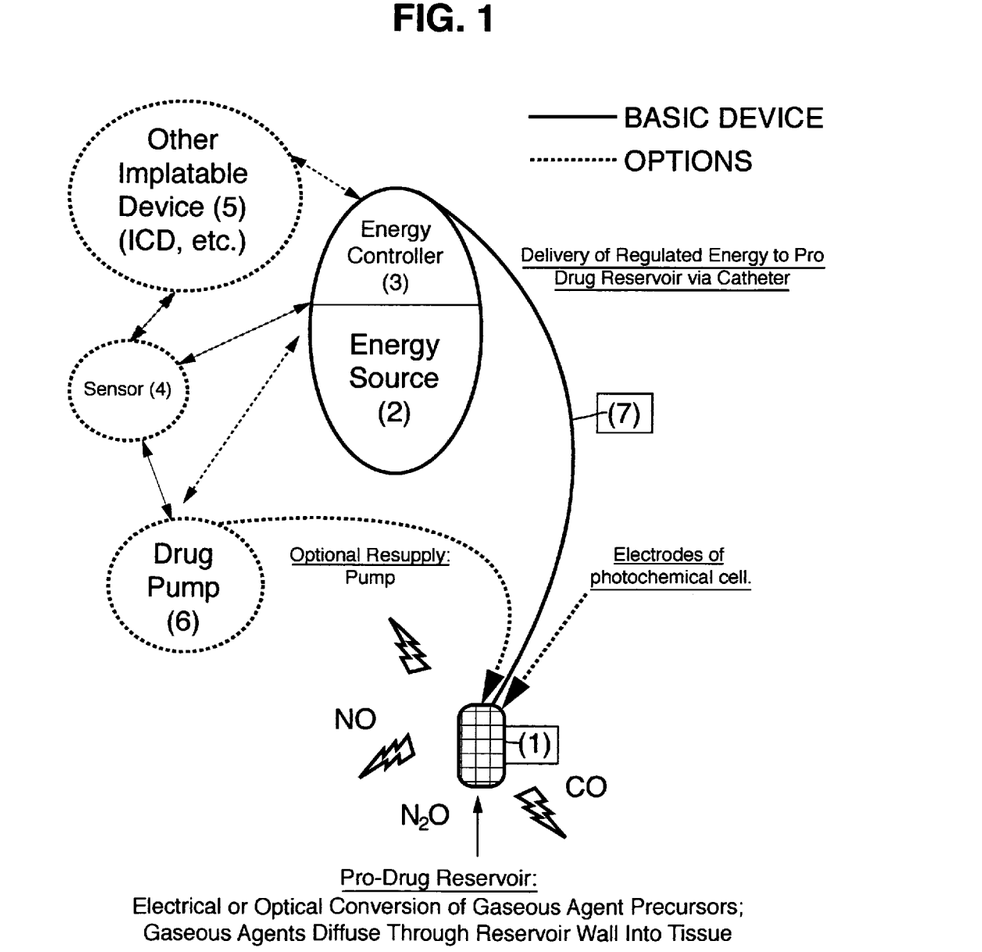
Figure 2:
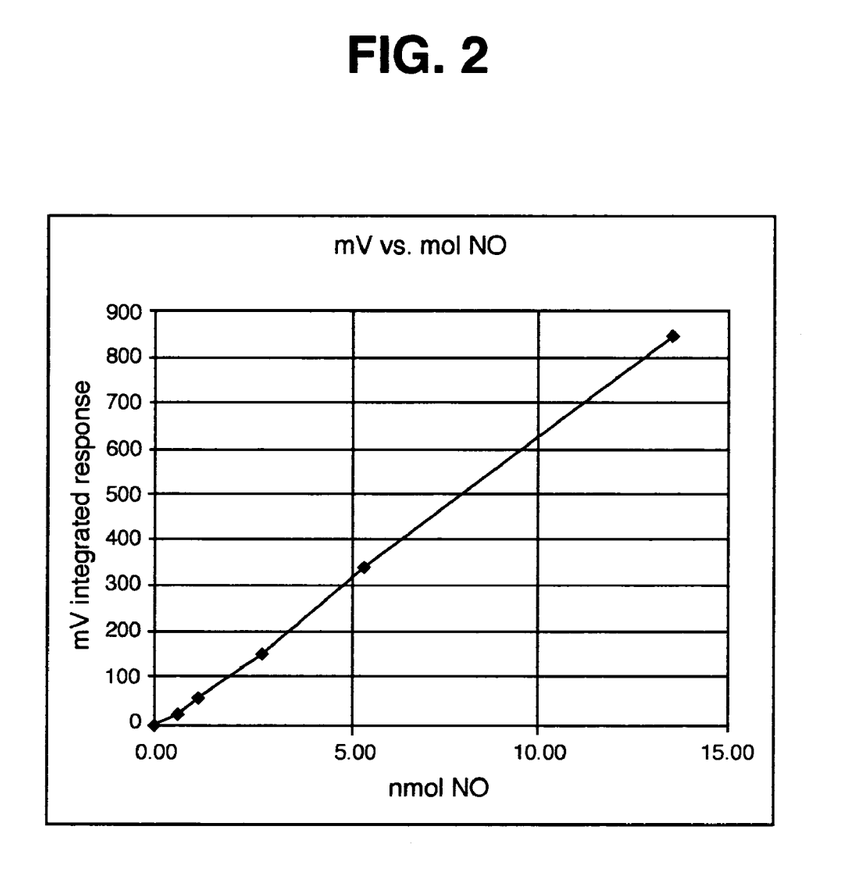
FIG. 2 (FIG. 2) shows NO electrochemical release form a electrochemical nitrite/ferrocyanide cell using a graphite electrode.

Using the small-scale electrochemical cell, an alkaline nitrite/ferro-ferricyanide solution was found to repeatedly generate nitric oxide with a potential of −0.6V when cycled between 0 and −1V. As seen FIG. 2, a linear relation was found between current (mV) integrated response and the amount of (nmoles) of NO produced.

Example 2

An example of an oxygen releasing, solid, self-driving cell is one in which the active anode material is $Ag_2O$ and the active cathode material is solid $I_2$ or a combination solid $I_2$ and poly(2-vinylpyridene) (P2VP) or poly 2 vinylquinoline (P2VQ) which combine to form a electrically and ionically conductive material. Several silver ion conductors are suitable as solid electrolytes for this application including $Ag_4 RbI_5$, $AgI/Al_2O_3$ and AgNasicon (Nasicon—(Na Super-Ionic Conductor)); however, the preferred electrolyte in this case is AgI which reactively forms at the interface between the anode ($Ag_2$ O) and cathode ($I_2$) layers. This electrolyte forms spontaneously as an interfacial reaction, requires no preparation, and conforms to any irregularities in the interface. The balanced electrochemical reactions is Such a cell has a standard potential, E° of 0.96 V; therefore, in this case, no battery or other applied voltage source is required to drive the process, only to close the electrical circuit. Once the electrical circuit is completed between the cathode and the anode, electrons and ions begin to flow and the device is operable. Other materials which would release oxygen when properly coupled with $I_2$ include $Na_2O$, $K_2 O$, $Na_2 O_2$, $Ag_2O_2$, $K_2O_2$, $Rb_2O$ and $Rb_2O_2$. The cell remains dormant until an electron conductor is connected between the anode and cathode materials.

Example 3

Another example of an oxygen releasing, solid cell which is self-driving is one in which the anode material is $Ag_2O$ and the cathode material is solid S or a combination of solid S and $Ag_2$ S which together form a material both electronically and ionically conductive. A suitable electrolyte is $Ag_4RbI_5$. The balanced electrochemical reactions is:

Such a cell has a standard potential, E° of 0.16 V. Other materials which could be used in the place of S are Se and Te.

Example 4

An example of a nitrogen releasing, solid, self-driving cell is one in which the anode material is $Li_3N$ and the cathode material is solid $I_2$ or a combination of solid $I_2$ and poly(2-vinylpyridene) which combine to form a material both electronically and ionically conductive. Several lithium ion conductors are suitable as solid electrolytes for this application including $LiI/Al_2O_3$ and Li-Nasicon; however, the preferred electrolyte in this case is LiI which forms at the interface between the anode and cathode layers. This electrolyte, similarly to AgI, forms spontaneously, requires no preparation, and conforms to any irregularities in the interface. The electrochemical reactions are:

Such a cell has a standard potential, E° of 2.16 V; therefore, in this case, no battery or other applied voltage source is required to drive the process. Once the anode and cathode are electronically connected, the cell will begin to function.

Example 5

Another example of a nitrogen releasing, solid, self-driving cell is one in which the anode material is $NaN_3$ and the cathode material is solid $I_2$ or a combination of solid $I_2$ and poly(2-vinylpyridene) which combine to form a material both electronically and ionically conductive. Several sodium ion conductors are suitable as solid electrolytes for this application including $NaI/Al_2O_3$ and Nasicon; however, the preferred electrolyte in this case is NaI which forms at the interface between the anode and cathode layers. This electrolyte forms spontaneously, requires no preparation, and conforms to any irregularities in the interface. The balanced electrochemical reaction is:

Such a cell has a standard potential, E° of 4.05 V; therefore, in this case, no battery or other applied voltage source is required to drive the process.

Example 6

Another example of a nitrogen releasing cell which is self driving is one in which the anode material is $Li_3N$ and the cathode material is polycarbon monofluoride of CFx (where x is 0.8 to 1.2). An example of such a material is a product of Allied Chemical under the trade name Accufluor©. A suitable electrolyte is a 1:1 mixture of ethylene glycol dimethyl ether and propylene carbonate containing 1M $LiBF_4$. This electrolyte is used with a thin microporous separator comprised of polypropylene or polyolefin. Such a separator is electronically insulative but has high ion permeability. The cell is similar to the Li—CFx battery described in Modern Battery Technology by C. D. S. Tuck, pp. 337-348, except that in the case of this invention, the lithium anode is replaced by a lithium nitride anode so that gas is released electrochemically as the cell discharges. The electrochemical reactions are:

$$x\ Li_3N + 3\ CF_x \rightarrow LiF + 3\ C + x/2\ N_2.$$

Such a cell has a standard potential, $E°$ of approximately, 2.7 V; therefore, in this case, no battery or other applied voltage source is required.

Example 7

Another example of an oxygen releasing cell which is self driving is one in which the anode material is $Ag_2O$ and the cathode material is polycarbon monofluoride of CFx (where x is 0.8 to 1.2). An example of such a material is a product of Allied Chemical under the trade name Accuflor®. A suitable electrolyte is 1:1 mixture of ethylene glycol dimethyl ether and propylene carbonate containing 1M $AgBF_4$. This electrolyte is used with a thin microporous separator comprised of polypropylene or polyolefin.

Example 8

Another example of an oxygen releasing cell which is self driving is one in which the anode material is a paste consisting of $Ag_2O$ silver nitrate and sodium hydroxide solution and the cathode material is a paste consisting of solid S, carbon, and silver nitrate, and where the anode and cathode are separated by a solid polymer electrolyte which has been exchanged with silver ion containing solution such as silver nitrate.

Example 9

The following examples illustrate different possibilities of the device where the solid anode and cathode couple require an applied voltage to drive the gas releasing reaction; such an applied voltage can be provided by one or more batteries:

An example of an oxygen releasing, solid cell which is not self-driving and which would require a battery or other applied voltage source is one in which the anode material is $Cu_2O$ and the cathode material is porous copper or graphite or carbon. Several copper ion conductors are suitable as solid electrolytes for this application including $Rb_4Cu_{16}I_7Cl_{13}$ or Cu-Nasicon or a mixture of CuI and $Al_2O_3$. The balanced electrochemical reaction is:

$$Cu_2O \rightarrow 2Cu + \tfrac{1}{2}O_2$$

Such a cell has a standard potential, $E°$ of −0.77 V. Other oxygen releasing solid couples. include $Cu_2O/I_2$, $Li_2O/I_2$, $Na_2O/S$, $K_2O_2/S$. Regardless of whether the cell is self-driven or driven with a battery or other applied voltage source, the rate of fluid dispensing is directly proportional to the rate of oxygen or nitrogen, in the above stated examples, released at the anode which is directly proportional to the electrical current.

What is claimed:

1. An implantable medical device for delivery of at least one gaseous agent to surrounding tissue, comprising:
    a. an energy storage component; and
    b. an implantable chemical cell, comprising:
       i. a reservoir containing at least one gaseous agent precursor, wherein said at least one gaseous agent precursor is supplied to said implantable chemical cell prior to implantation of said implantable chemical cell;
       ii. an energy interface operably linked to said at least one gaseous agent precursors; and
       iii. a gaseous agent dispensing interface for dispensing said at least one gaseous agents produced in said chemical cell;
    wherein said energy source provides energy at the interface of said chemical cell to convert said at least one gaseous agent precursors into said at least one gaseous agents, wherein said at least one gaseous agent is delivered to the surrounding tissue from said gaseous agent dispensing interface.

2. The implantable medical device of claim 1, wherein the energy source provides an electrical voltage through a pair of biocompatible electrical leads.

3. The implantable medical device of claim 1, wherein the energy source provides light.

4. The implantable medical device of claim 1, wherein the implantable chemical cell is an electrochemical cell.

5. The implantable medical device of claim 1, wherein the implantable chemical cell is a photochemical cell.

6. The implantable medical device of claim 1, further comprising an energy controlling component.

7. The implantable medical device of claim 1, wherein said at least one gaseous agent is selected from the group consisting of $O_2$, $O_3$, NO, $N_2O$, CO, $CO_2$, $H_2S$, $NH_3$, $H_2O_2$ and $SF_6$.

8. The implantable medical device of claim 1, wherein said energy interface is a pair of electrodes.

9. The implantable medical device of claim 1, wherein said energy interface is a light dispensing cell.

10. The implantable medical device of claim 1, wherein the gaseous agent dispensing interface comprises a gas-permeable material.

11. The implantable medical device of claim 1, further comprising a mechanism for controllably delivering said at least one gaseous agent.

12. The implantable medical device of claim 1, wherein said at least one gaseous agent is selected from the group consisting of NO, $NO_2$, $O_2$, and CO.

13. The implantable medical device of claim 1, further comprising a drug pump for resupplying said at least one gaseous agent precursors to said implantable chemical cell.

14. The implantable medical device of claim 1, further comprising a sensor for controlling the delivery of said at least one gaseous agent.

15. A method of treating a patient comprising delivering at least one gaseous agent from the implantable medical device of claim 1 to said surrounding tissue.

16. The method of claim 15, wherein said at least one gaseous agent is selected from the group consisting of NO, $NO_2$, $O_2$, and CO.

17. The method of claim 15, wherein the delivery of said at least one gaseous agent has a therapeutic use selected from the group consisting of delivery of oxygen to oxygen depleted tissues, minimizing ischemia in an organ, improving efficacy of anticancer therapy, anesthetizing a patient, reversing hypoxia in a tissue, treating angina, preventing or slowing restenosis following balloon angioplasty, treating impotence, preventing or delaying pre-term labor, treating asthma and other lung dysfunction, preventing or decreasing the severity of stroke, preventing or decreasing memory loss due to trauma or neurodegenerative diseases, treating Parkinson's disease or epilepsy, stimulating angiogensis, and promoting site-specific healing or tissue development.

* * * * *

UNITED STATES PATENT AND TRADEMARK OFFICE
CERTIFICATE OF CORRECTION

PATENT NO. : 7,122,027 B2  
APPLICATION NO. : 10/155296  
DATED : October 17, 2006  
INVENTOR(S) : Paul V. Trescony et al.

It is certified that error appears in the above-identified patent and that said Letters Patent is hereby corrected as shown below:

Col. 12, Line 19:   ...agents...   should read   ...agent...

Signed and Sealed this

Eleventh Day of December, 2007

JON W. DUDAS  
*Director of the United States Patent and Trademark Office*

UNITED STATES PATENT AND TRADEMARK OFFICE
CERTIFICATE OF CORRECTION

PATENT NO. : 7,122,027 B2
APPLICATION NO. : 10/155296
DATED : October 17, 2006
INVENTOR(S) : Paul V. Trescony et al.

It is certified that error appears in the above-identified patent and that said Letters Patent is hereby corrected as shown below:

Col. 12, Line 19: ...agents... should read ...agent...

Signed and Sealed this

Twenty-fifth Day of December, 2007

JON W. DUDAS
*Director of the United States Patent and Trademark Office*